United States Patent [19]
Payne, Jr., deceased

[11] 3,958,006

[45] May 18, 1976

[54] CARBAMATE PESTICIDAL COMPOSITIONS

[75] Inventor: Linwood K. Payne, Jr., deceased, late of Charleston, W. Va., by Betty Lou B. P. Payne, executrix

[73] Assignee: Union Carbide Corporation, New York, N.Y.

[22] Filed: Mar. 6, 1974

[21] Appl. No.: 448,699

Related U.S. Application Data

[62] Division of Ser. No. 252,329, May 10, 1972, Pat. No. 3,849,478.

[52] U.S. Cl. .................................................. 424/300
[51] Int. Cl.² ....................... A01N 9/12; A01N 9/20

[58] Field of Search ..................................... 424/300

[56] References Cited
UNITED STATES PATENTS

| | | | |
|---|---|---|---|
| 3,597,472 | 8/1971 | Heiss et al. ........................... | 260/479 |
| 3,726,911 | 4/1973 | Degginger et al. ................... | 260/479 |

*Primary Examiner*—Sam Rosen
*Assistant Examiner*—D. W. Robinson
*Attorney, Agent, or Firm*—Robert C. Brown

[57] ABSTRACT

4-Substituted-5,6,7,8-tetrahydro-1-naphthyl-N-methylcarbamates have been found to exhibit exceptional insecticidal activity.

5 Claims, No Drawings

CARBAMATE PESTICIDAL COMPOSITIONS

This is a division of application Ser. No. 252,329 filed May 10, 1972 now U.S. Pat. No. 3,849,478.

This invention relates to methods and compositions for combating insects. In another aspect, this invention relates to certain specifically substituted 5,6,7,8-tetrahydro-1-naphthyl methylcarbamate compositions which are novel per se.

The compounds which are employed as the active ingredients in the pesticidal compositions of this invention are 4-substituted-5,6,7,8-tetrahydro-1-naphthyl methylcarbamate compounds corresponding to the following general formula:

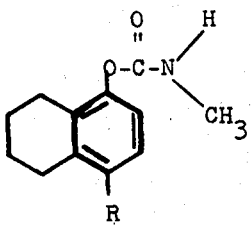

I wherein R is:

| | |
|---|---|
| amino | $-NH_2$ |
| lower alkyl amino | $-NHR'$ |
| dilower alkyl amino | $-NR'_2$ |
| formamido | $-NH-COH$ |
| lower acylamido | $-HN-COR'$ |
| arylcarboxamido | $-NH-COA_r$ |
| lower alkylideneimino | $-N=CHR'$ |
| dilower alkylamino lower alkylene imino | $-N=A-NR'_2$ |
| lower alkylureido | $-NH-CO-NHR'$ |
| dilower alkylureido | $-NH-CO-NR'_2$ |
| lower alkoxy | $-OR$ |
| lower aralkoxy | $-O-A-A_r$ |
| lower alkylthio | $-SR'$ |
| lower aralkylthio | $-S-A-A_r$ |
| lower alkyl sulfinyl | $-SO-R'$ |
| lower alkyl sulfonyl | $-SO_2-R'$ |
| halogen | $-Cl, -Br, -F$ |
| nitro | $-NO_2$ | where R' is lower alkyl, A is lower alkylene and $A^R$ is a substituted or unsubstituted monocyclic hydrocarbon ring. Aromatic substituents may be substituted with any essentially inert substituents such as halogen, nitro, lower alkyl, lower alkoxy, lower haloalkyl or aralkoxy groups.

The novel compositions of this invention are those conforming to the following generic formula:

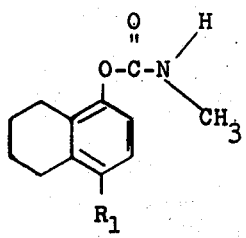

II wherein $R_1$ is:

| | |
|---|---|
| formamido | $-NH-COH$ |
| lower acylamido | $-NH-COR'$ |
| arylcarboxamido | $-NH-COA_r$ |
| lower alkylideneimino | $-N=CHR'$ |
| dilower alkylamino lower alkylene imino | $-N=A-NR'_2$ |
| lower alkylureido | $-NH-CO-NHR'$ |
| dilower alkylureido | $-NH-CO-NR'_2$ |
| lower alkoxy | $-OR$ |
| lower aralkoxy | $-O-A-A_r$ |
| lower alkylthio | $-SR'$ |
| lower aralkylthio | $-S-A-A_r$ |
| lower alkyl sulfinyl | $-SO-R'$ |
| lower alkyl sulfonyl | $-SO_2-R'$ |
| halogen | $-Cl, -Br, -F$ |
| nitro | $-NO_2$ | where R' is lower alkyl, A is lower alkylene and $A_r$ is a substituted or unsubstituted monocyclic hydrocarbon ring. Aromatic substituents may be substituted with any essentially inert substituents such as halogen, nitro, lower alkyl, lower alkoxy, lower haloalkyl or aralkoxy groups.

Illustrative of the new compositions of this invention are the following:

4-formamido-5,6,7,8-tetrahydro-1-naphthyl-N-methylcarbamate 4-methylcarboxamido-5,6,7,8-tetrahydro-1-naphthyl-N-methylcarbamate 4-phenylcarboxamido-5,6,7,8-tetrahydro-1-naphthyl-N-methylcarbamate 4-(p-chlorophenylcarboxamido)-5,6,7,8-tetrahydro-1-naphthyl-N-methylcarbamate 4-(2',4'-dibromophenylcarboxamido)-5,6,7,8-tetrahydro-1-naphthyl-N-methylcarbamate 4-(p-methylphenylcarboxamido)-5,6,7,8-tetrahydro-1-naphthyl-N-methylcarbamate 4-(p-trifluoromethylphenylcarboxamido)-5,6,7,8-tetrahydro-1-naphthyl-N-methylcarbamate 4-methylethylideneimino-5,6,7,8-tetrahydro-1-naphthyl-N-methylcarbamate 4-dimethylaminomethyleneimino-5,6,7,8-tetrahydro-1-naphthyl-N-methylcarbamate 4-methylureido-5,6,7,8-tetrahydro-1-naphthyl-N-methylcarbamate 4-dimethylureido-5,6,7,8-tetrahydro-1-naphthyl-N-methylcarbamate 4-methoxy-5,6,7,8-tetrahydro-1-naphthyl-N-methylcarbamate 4-isobutoxy-5,6,7,8-tetrahydro-1-naphthyl-N-methylcarbamate 4-benzyloxy-5,6,7,8-tetrahydro-1-naphthyl-N-methylcarbamate 4-(p-nitrobenzyloxy)-5,6,7,8-tetrahydro-1-naphthyl-N-methylcarbamate 4-(p-methoxybenzyloxy)-5,6,7,8-tetrahydro-1-naphthyl-N-methylcarbamate 4-methylthio-5,6,7,8-tetrahydro-1-naphthyl-N-methylcarbamate 4-benzylthio-5,6,7,8-tetrahydro-1-naphthyl-N-methylcarbamate 4-methylsulfinyl-5,6,7,8-tetrahydro-1-naphthyl-N-methylcarbamate 4-methylsulfonyl-5,6,7,8-tetrahydro-1-naphthyl-N-methylcarbamate 4-chloro-5,6,7,8-tetrahydro-1-naphthyl-N-methylcarbamate 4-bromo-5,6,7,8-tetrahydro-1-naphthyl-N-methylcarbamate 4-fluoro-5,6,7,8-tetrahydro-1-naphthyl-N-methylcarbamate 4-nitro-5,6,7,8-tetrahydro-1-naphthyl-N-methylcarbamate These compositions can be conveniently prepared by reacting an appropriately substituted 5,6,7,8-tetrahydro-1-naphthol with methyl isocyanate in accordance with the following general reaction scheme:

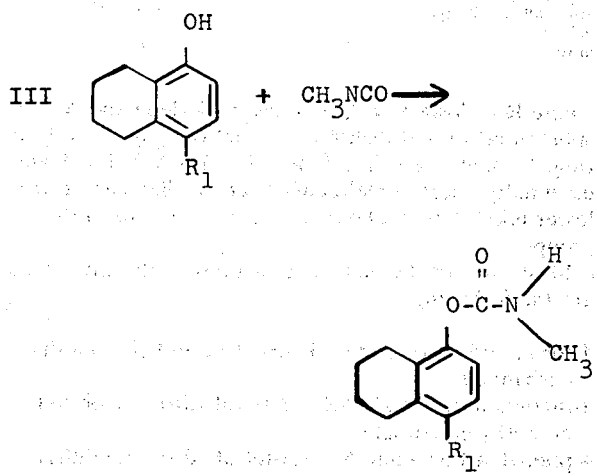

wherein $R_1$ is as defined above.

The composition where $R_1$ is amino is prepared by hydrolyzing an alkylideneimino derivative. The lower alkylamino derivatives are prepared by hydrogenation of the corresponding alkylideneimino derivative. The alkylideneimino naphthol precursor is prepared by reacting 4-aminonaphthol with an appropriate aldehyde. The 4-acylamido and 4-arylcarboxamido naphthols are prepared by the reaction of the appropriate acid halide or anhydride with 4-aminonaphthol. The alkyl ureido derivatives are prepared by reacting 4-aminonaphthol with methylisocyanate simultaneously producing the carbamate. The dialkyl ureido naphthols are prepared by reacting dimethyl carbamoyl chloride with 4-aminonaphthol. The alkyl sulfinyl and alkyl sulfonyl substituted compounds are prepared by oxidation of the corresponding lower alkyl thionaphthylcarbamate compound.

The conversion of the 1-naphthol composition to the corresponding n-methylcarbamate is preferably conducted in an inert solvent at ambient temperature but can be carried out at temperatures of from $-10°$ to $100°C$. To increase yields and to reduce reaction time it is preferred to conduct this reaction in the presence of a suitable catalyst such as 1,4-diazadicyclo(2.2.2-octane), trimethylamine, triethylamine or dibutyltin diacetate, although in some instances no catalyst is required.

The following examples are presented to more clearly illustrate the procedures used for preparing the compounds used in the practice of this invention.

EXAMPLE I

Preparation of 4-Chloro-5,6,7,8-tetrahydro-1-naphthol

A solution of 37 grams (0.25 mole) of 5,6,7,8-tetrahydronaphthol in 200 ml of carbon tetrachloride was treated dropwise with stirring with 33.8 grams (0.25 mole) of sulfuryl chloride at room temperature. When addition was complete the reaction mixture slowly brought to boiling over a 1 hour period and held there at reflux for 30 minutes. After cooling to ambient temperature the reaction mixture was washed with 10 percent aqueous sodium carbonate and then with water. After drying over calcium chloride the carbon tetrachloride solution was distilled to give a portion, b.p. 110°-112/0.25 mm, which was recrystallized from hexane to give 8 grams (17.5 percent) of product, m.p. 58°-59°C.

EXAMPLE II

Preparation of 4-Chloro-5,6,7,8-tetrahydro-1-naphthyl-N-methylcarbamate

4-Chloro-5,6,7,8-tetrahydro-1-naphthol (recrystallized from hexane; m.p. 58°-59°) was dissolved in dry acetone and treated with a slight molar excess of methyl isocyanate, in the presence of a catalytic amount of 1,4-diazabicyclo(2.2.2)octane for 2 days at room temperature. Evaporation of the solvent resulted in a crystalline residue which when recrystallized from isopropyl alcohol-water melted at 142°-144°. The yield was 82% of theory.

Anal. Calc'd. for $C_{12}H_{14}ClNO_2$: C, 60.1; H, 5.9; N, 5.8. Found: C, 60.4; H, 6.1; N, 6.1.

Infrared: Carbamate N—H at $3.0\mu$ and $6.52\mu$; carbamate C=O at $5.8\mu$ and $5.88\mu$ and carbamate C—O at $7.87\mu$ and $8.0\mu$.

EXAMPLE III

Preparation of 4-Bromo-5,6,7,8-tetrahydro-1-naphthol

To a solution of 37 grams (0.25 mole) of 5,6,7,8-tetrahydronaphthol in 150 ml of carbon tetrachloride was added dropwise with stirring a solution of 44 grams (0.25 mole) of bromine in 50 ml of carbon tetrachloride. When the addition was complete the mixture was stirred for 30 minutes at room temperature and then evaporated in vacuo to a residue which after two recrystallizations from hexane provided 13 grams (22.9 percent) of product, m.p. 83°-85°C.

Anal. Calc'd. for $C_{10}H_{11}BrO$: C, 52.86; H, 4.88. Found: C, 52.99; H, 4.73.

EXAMPLE IV

Preparation of 4-Bromo-5,6,7,8-tetrahydro-1-naphthyl-N-methylcarbamate

4-Bromo-5,6,7,8-tetrahydro-1-naphthol (recrystallized from hexane; m.p. 83°-85°) was converted to the N-methylcarbamate by the method described in Example II for the chloro analog in 88% yield; m.p. 155-156 (isopropyl alcohol-water).

Anal. Calc'd. for $C_{12}H_{14}BrNO_2$: C, 50.7; H, 5.0; N, 4.9. Found: C, 51.3; H, 5.1; N, 5.3.

Infrared: Carbamate N—H at $3.0\mu$ and $6.52\mu$, carbamate C=O at $5.8\mu$ and $5.88\mu$ and carbamate C—O at $7.81\mu$ and $8.03\mu$.

EXAMPLE V

Preparation of 4-Methylmercapto-5,6,7,8-tetrahydro-1-naphthyl-N-methylcarbamate

Dimethyl disulfide (23.6g; 0.25 mole) was added to a stirred flask containing 100 ml. of carbon tetrachloride cooled to $-15°$. Chlorine (17g; 0.25 mole) was then added with stirring at $-15°$ during 1 hour. The solution was allowed to gradually warm to $0°$ and added dropwise to 74g (0.5 mole) of 5,6,7,8-tetrahydro-1-naphthol in 100 ml. of carbon tetrachloride at 15°. The mixture The then stirred overnight at room temperature. An unidentified product precipitated during this time which was removed by filtration. Distillation of the filtrate resulted in 40g. of unreacted tetrahydronaphthol, 40g. of a midcut and 10g. of 4-methylthio-5,6,7,8-tetrahydro-1-naphthol which was taken as a residue. Recrystallization of this residue from a large volume of cyclohexane resulted in a white solid; m.p. 120°–122°.

Anal. Calc'd. for $C_{11}H_{14}OS$: S, 16.5. S, 16.5.

Infrared: O—H at $3.05\mu$ and aromatic C—O—at $8.0\mu$, 1,2,3,4-tetrasubstituted benzene C—H bending at $12.35\mu$ and $12.5\mu$ and C—S—C and $14.8\mu(?)$.

Reaction of this methylmercaptophenol with methyl isocyanate by the method described in Example II for the chloro analog resulted in an 80 percent yield of 4-methylmercapto-5,6,7,8-tetrahydro-1-naphthyl N-methylcarbamate; m.p. 146°–147° (xylene).

Anal. Calc'd. for $C_{13}H_{17}NO_2S$: C, 62.1; H, 6.8; N, 5.6. Found: C, 62.3; H, 7.0, N, 5.3.

EXAMPLE VI

Preparation of 4-Methylsulfinyl-5,6,7,8-tetrahydro-1-naphthyl N-methylcarbamate This compound was prepared in 90% yield by allowing a solution of 4-methylmercapto-5,6,7,8-tetrahydro-1-naphthyl N-methylcarbamate in ethyl acetate to slowly react at 35°–40° with one equivalent of peracetic acid in ethyl acetate. An ice bath was required to maintain the reaction temperature in the proper range. At the conclusion of the reaction, the solution was diluted with heptane and the resulting precipitate collected by filtration and washed thoroughly with heptane. After drying, the product melted at 135°–138°.

Anal. Calc'd. for $C_{13}H_{17}NO_3S$: C, 58.4; H, 6.4; N, 5.2. Found: C, 58.4; H, 6.3; N, 5.6.

Infrared: Carbamate N—H at $3.1\mu$ and $6.41\mu$; C=O at $5.81\mu$; C—O at $8.15\mu$; S=O at $9.05\mu$.

EXAMPLE VII

Preparation of 4-Methylsulfonyl-5,6,7,8-tetrahydro-1-naphthyl N-methylcarbamate This compound was prepared in 90% yield using the method described for the sulfoxide analog, except that two equivalents of peracetic acid were required. The product which precipitated upon dilution of the ethyl acetate solution with n-heptane was purified by recrystallization from xylene; m.p. 162°–164°.

Anal. Calc'd. for $C_{13}H_{17}NO_4S$: C, 55.1; H, 6.0; N, 4.9. Found: C, 55.4; H, 6.1; N, 5.0.

EXAMPLE VIII

Preparation of 4-Formamido-5,6,7,8-tetrahydro-1-naphthyl N-methylcarbamate a. 5,6,7,8-tetrahydro-1-naphthol (59g; 0.5 mole) dissolved in 350 ml. of isopropyl alcohol was treated slowly with 167 ml. (2.0 mole) of concentrated hydrochloric acid while stirring at 0°. The resulting solution was then treated with a solution of 30g. (0.44 mole) of sodium nitrite in 100 ml. of water. The addition was conducted over a period of 1 hour and the well-stirred mixture maintained at 0° with the aid of an ice bath. One-half hour after the sodium nitrite feed was completed the reaction mixture was poured into 2 liters of iced water. A light brown solid precipitated and was collected by filtration. After washing thoroughly with water and drying, the solid melted at 150°. Recrystallization from ethanol raised the melting point to 159°–160°. Further recrystallization from xylene increased it to 167°–168°. The yield was 40g.

Anal. Calc'd. for $C_{10}H_{11}NO_2$: C, 67.8; H, 6.3; N, 7.9. Found: C, 68.0; H, 6.4; N, 8.1.

Infrared: High resolution IR of $3\mu$ region shows only one absorption band at $2.793\mu$ indicative of an oxime. No evidence of aromatic O—H at $2.77\mu$. Conj. C=O at $6.13\mu$; C=N at $6.45\mu$ and C=N—O at $10.55\mu$.

b. Twenty-five grams of 5,6,7,8-tetrahydro-1,4-naphthoquinone monoxime was dissolved in 250 ml. of isopropyl alcohol, 7g. of Raney nickle catalyst added and the mixture hydrogenated at 40–50 psi. After 45 minutes hydrogen uptake was complete. The catalyst was removed by filtration, the solvent evaporated and the residue recrystallized from toluene. There was obtained 15g. of 4-amino-5,6,7,8-tetrahydro-1-naphthol; m.p. 144°–146°.

Anal. Calc'd. for $C_{10}H_{13}NO$: C, 73.6; H, 8.0; N, 8.6. Found: C, 73.5; H, 8.1; N, 8.5.

Infrared: $NH_2$ at $2.95\mu$ and $3.02\mu$; bonded O—H at $3.20\mu$, $3.70\mu$ and $3.86\mu$; aromatic C—O at $7.72\mu$.

c. Ten grams of 4-amino-5,6,7,8-tetrahydro-1-naphthol and 40 ml. of 88% formic acid were heated at 108° for 90 minutes. The mixture was cooled and added to 300 ml. of cold water. The solid which formed was filtered and recrystallized from an isopropyl alcohol-water (1:1) mixture. There was obtained 10g. of 4-formamido-5,6,7,8-tetrahydro-1-naphthol; 175°–176°.

Anal. Calc'd. for $C_{11}H_{13}NO_2$: C, 69.1; H, 6.9; N, 7.3 Found: C, 69.6; H, 6.7; N, 7.6

Infrared: $3.08\mu$ and $3.15\mu$ N—H and O—H; C=O at $6.11\mu$; aromatic C—O— at $7.87\mu$.

d. 4-Formamido-5,6,7,8-tetrahydro-1-naphthol was dissolved in anhydrous acetone and allowed to react with an excess of methyl isocyanate in a pressure bottle at room temperature for 2 days. Triethylamine was used as a catalyst. The solvent was stripped from the product under reduced pressure and the solid residue washed thoroughly with isopropyl ether. There was obtained 4-formamido-5,6,7,8-tetrahydro-1-naphthyl N-methylcarbamate, m.p. 165°–166°, in 87% yield.

Anal. Calc'd. for $C_{13}H_{16}N_2O_3$: C, 62.9; H, 6.5; N, 11.3. Found: C, 62.9; H, 6.6; N, 11.5.

EXAMPLE IX

Preparation of 4-Dimethylamino-5,6,7,8-tetrahydro-1-naphthyl N-methylcarbamate 15g. (0.1 mole) of 4-Amino-5,6,7,8-tetrahydro-1-naphthol prepared by the method described in Example VIII in 50 ml. of ethyl acetate was added to a stirred flask along with 25g. (0.3 mole) of sodium bicarbonate and 50 ml. of water. The well stirred mixture was then treated dropwise with 32g. (0.25 mole) was dimethyl sulfate. The reaction temperature was maintained at 23°–28° during the addition of the dimethyl sulfate and for about 3 hours thereafter. Then 10 ml. of ammonium hydroxide was added to decompose any unreacted dimethyl sulfate and the mixture diluted with 100 ml. of chloroform. The organic layer was washed thoroughly with water and the solvent evaporated. The residue was recrystallized from heptane to give 12g. of 4-dimethylamino-5,6,7,8-tetrahydro-1-naphthol; m.p. 73°–75°.

Anal. Calc'd. for $C_{12}H_{17}NO$: C, 75.3; H, 9.0; N, 7.3. Found: C, 74.7; H, 9.2; N, 7.1.

Infrared: O—H at $2.96\mu$; N—$CH_3$ at $3.63\mu$; aromatic C—O— at $7.83\mu$.

NMR: O—H broad singlet at 5.56 ppm; aromatic AB pair at 6.47 ppm and 6.80 ppm; $N(CH_3)_2$ at 2.60 ppm along with benzylic hydrogens at 2.65 ppm.

4-Dimethylamino-5,6,7,8-tetrahydro-1-naphthol (9.6g; 0.05 mole) dissolved in 50 ml of dry acetone was treated with methyl isocyanate (3.1g.; 0.055 mole) and 2 drops of triethylamine in a pressure bottle for 30 hours at room temperature. The solvent was evaporated under reduced pressure and the resulting solid recrystallized from heptane to afford 11g. of 4-dimethylamino-5,6,7,8-tetrahydro-1-naphthyl methylcarbamate, m.p. 97°–101°.

Anal. Calc'd. for $C_{14}H_{20}N_2O_2$: C, 67.7; H, 8.1; N, 11.3. Found: C, 67.1; H, 8.0; N, 11.7.

Infrared: N—H at $2.95\mu$ and $6.62\mu$; C=O at $5.85\mu$; C—O at $8.0\mu$ and $8.15\mu$.

A series of compounds representative of the compounds useful according to our invention were evaluated for pesticidal activity.

The compounds were evaluated with respect to their contact and systemic activity against respective insects, viz., two spotted spider, mite, bean, aphid, southern armyworm, Mexican bean beetle, and house fly, by the following standard procedures.

Suspensions of the test compounds were prepared by dissolving 1 gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 per cent by weight of compound. The test concentrations employed in the tests described hereinbelow was obtained by diluting the stock suspension with water. Serial dilution tests were carried out in the indicated instances to determine the $LD_{50}$ (concentration of chemical required to kill 50 per cent of the insect population) values for each test compound. The test procedures were as follows:

Bean Aphid Foliage Spray Test

Adults and nymphal stages of the bean aphid (*Aphis fabae Scop.*), reared on potted dwarf nasturtium plants at 65°–70°F. and 50–70 per cent relative humidity, constituted the test insects. For testing purposes, the number of aphids per pot was standardized to 100–150 by trimming plants containing excess aphids. The test compounds were formulated by diluting the stock suspension with water to give a suspension containing 100 parts of test compound per million parts of final formulation, by weight. The potted plants (one pot per compound tested), infested with 100–150 aphids, were placed on a revolving turntable and sprayed with 100–110 milliliters of test compound formulation by use of a DeVilbiss spray gun set at 40 psig. air pressure. This application, which lasted 30 seconds, was sufficient to wet the plants to run-off. As a control, 100–110 milliliters of water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24-hour holding period were 65°–70°F. and 50–70 per cent, respectively. Aphids which fell onto the paper and were unable to remain standing after being uprighted were considered dead. Aphids remaining on the plants were observed closely for movement and those which were unable to move the length of the body upon stimulation by prodding were considered dead. Per cent morality was recorded for various concentration levels.

Southern Armyworm Leaf Dip Test

Larvae of the southern armyworm (*Prodenia eridania* (Cram.)), reared on Tendergreen bean plants at a temperature of 80±5°F. and a relative humidity of 50±5 per cent, constituted the test insects. The test compounds were formulated by diluting the stock suspension with water to give s suspension containing 500 parts of test compound per million parts of final formulation (by weight). Paired seed leaves, excised from Tendergreen bean plants, were dipped in the test formulations until thoroughly wetted, excess liquid being removed by gentle shaking. While the leaves were drying in a ventilated hood, wilting was prevented by placing the stems in water. When dry, the paired leaves were separated and each one was placed in a 9-centimeter Petri dish lined with moistened filter paper. Five randomly selected larvae were introduced into each dish and the dishes were closed. The closed dishes were labeled and held at 80°–85°F. for 3 days. Although the larvae could easily consume the whole leaf within 24 hours, no more food was added. Larvae which were unable to move the length of the body, even upon stimulation by prodding, were considered dead. Per cent mortality was recorded for various concentration levels.

Mexican Bean Beetle Leaf Dip Test

Third instar Larvae of the Mexican bean beetle (*Epilachna varivestis Muls.*), reared on Tendergreen bean plants at a temperature of 80±5°F. and 50±5 per cent relative humidity, were the test insects. The test compounds were formulated by diluting the stock suspension with water to give a suspension containing 100 parts of test compound per million parts of final formulation by weight. Paired seed leaves excised from Tendergreen bean plants were dipped in the test formulation until thoroughly wetted, excess liquid being removed by gentle shaking. While the leaves were drying under a hood, wilting was prevented by placing the stems in water. When dry, the paired leaves were separated and each was placed in a 9-centimeter Petri dish lined with moistened filter paper. Four randomly selected larvae were introduced into each dish, and the dishes were closed. The closed dishes were labeled and held at a temperature of 80±5°F. for 3 days. Although the larvae could easily consume the lef within 24 to 48 hours, no more food was added. Larvae which were unable to move the length of the body, even upon stimulation, were considered dead. Per cent mortality was recorded for various concentration levels.

Fly Bait Test 50±

Four to 6 day old adult house flies (*Musca domestica L.*), reared according to the specifications of the Chemical Specialties Manufacturing Association (Blue Book, McNair-Dorland Co., N.Y. 1954; pages 243–244, 261) under controlled conditions of 80±5°F. and 5035 5 per cent relative humidity, were the test insects. The flies were immobilized by anesthetizing with carbon dioxide and 25 immobilized individuals, males and females, were transferred to a cage consisting of a standard food strainer about 5 inches in diameter which was inverted over brown wrapping paper. The test compounds were formulated by diluting the stock suspension with a 10 per cent (by weight) sugar solution to give a suspension containing 500 parts of test compound per million parts of final formulation, by weight. Ten milliliters of the test formulation were added to a souffle cup containing a 1-inch square of an absorbent pad. This bait cup was introduced and centered on the blotting paper under the food strainer prior to admitting the flies. The caged flies were allowed to feed on the bait for 24 hours, at a temperature of 80±5°F. and the relative humidity of 50±5 per cent. Flies which showed no sign of movement on prodding were considered dead. Per cent mortality was recorded for various concentration levels.

Mite Ovicide Test

The test organism was the egg of the two-spotted mite (*Tetranychus Urticae Koch*), as obtained from adults reared on Tendergreen bean plants under controlled conditions of 80±5°F. and 50±5 per cent relative humidity. Heavily infested leaves from a stock culture were placed on the primary leaves of 2 bean plants 6 to 8 inches in height, growing in a 2½ inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on plants infested with eggs. The sprayed plants were held at 80±5°F. and 50±5 per cent relative humidity for 6 days, after which a microscopic examination was made of unhatched (dead) and hatched (living) eggs. Percent mortality was recorded for various concentration levels.

The results of these tests are set forth in Table I below. All of these compounds conform to generic formula I above; with the R substituents as indicated in the table below.

TABLE I

| R= | Insecticidal Activity, $LD_{50}$ ppm* | | | |
| --- | --- | --- | --- | --- |
|  | Bean Aphid | Army Worm | Mite | Mexican Bean Beetle | House-Fly |
| —$NH_2$ | 5 | 250 | — | 100 | — |
| —$N(CH_3)_2$ | 1 | 85 | 300 | 6 | 200 |
| —$N(C_2H_5)_2$ | 2 | 62 | — | 3 | — |
| —$SCH_3$ | — | 500 | — | 30 | — |
| —SO—$CH_3$ | — | — | — | 125 | 50 |
| —$SO_2$—$CH_3$ | — | — | — | >100 | — |
| —N(H)—COH | — | 180 | 500 | 25 | 90 |
| —Cl | — | 500 | 500 | 20 | — |
| —Br | — | 500 | 500 | 60 | — |
| —$NO_2$ | 100 | 500 | — | — | — |
| —N=CH—$N(CH_3)_2$ | 8 | 500 | 100 | 40 | 40 |
| —N=CHCH($CH_3$)$_2$ | 27 | 450 | — | 100 | — |

*dashes indicate the absence of significant activity

It will be understood that the insect species employed in the above tests are merely representative of a wide variety of pests that can be controlled by use of our compounds. For example, the hornworm, cabbage worm, corn ear worm, and Colorado potato beetle can also be combated with our compounds.

The compounds contemplated in this invention may be applied as insecticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a non-phytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 per cent by weight and in the solid formulations from about 0.5 to about 90 per cent by weight. Satisfactory sprays, dusts, or granules for general use contain from about ¼ to 15 pounds of active toxicant per acre.

The pesticides contemplated herein prevent attack by insects upon plants or other material to which the pesticides are applied, and they have high residual toxicity. With respect to plants they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable insecticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants, yet by root uptake they will kill the pests feeding thereon.

What is claimed is:

1. A pesticidal composition comprising an acceptable carrier and, as an active toxicant an insecticidally effective amount of a compound of the formula:

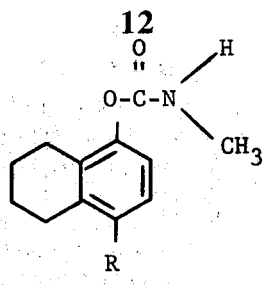

wherein R is an amino, lower alkyl amino, dilower alkyl amino, formamido, lower acylamido, phenylcarboxamido, lower alkylideneimino, dilower alkylamino, lower alkyleneimino, lower alkylureido, dilower alkylureido, lower phenylalkoxy, lower alkylthio, lower phenylalkylthio, lower alkyl sulfinyl, and lower alkyl sulfonyl.

2. The pesticidal composition of claim 1 wherein R is an amino, lower alkylamino or dilower alkylamino group.

3. The pesticidal composition of claim 1 wherein the active toxicant is 4-amino-5,6,7,8-tetrahydro-1-naphthyl-N-methylcarbamate.

4. The pesticidal composition of claim 1 wherein the active toxicant is 4-formamido-5,6,7,8-tetrahydro-1-naphthyl-N-metnhylcarbamate.

5. The pesticidal composition of claim 1 wherein the active toxicant is 4-dimethylaminomethyleneimino-5,6,7,8-tetrahydro-1-naphthyl-N-methylcarbamate.

* * * * *

UNITED STATES PATENT OFFICE
CERTIFICATE OF CORRECTION

Patent No. 3,958,006                    Dated May 18, 1976

Inventor(s) L.K. Payne, Jr.

It is certified that error appears in the above-identified patent and that said Letters Patent are hereby corrected as shown below:

COLUMN 5, LINES 2-3, "The mixture the then" SHOULD READ

"The mixture was then".

COLUMN 8, LINE 23, "s" SHOULD READ "a".

COLUMN 9, LINE 8, "5035 5" SHOULD READ "$50\pm5$".

Signed and Sealed this

Twenty-seventh Day of July 1976

[SEAL]

Attest:

RUTH C. MASON
*Attesting Officer*

C. MARSHALL DANN
*Commissioner of Patents and Trademarks*